USO05562684A

United States Patent [19]

Kammerer

[11] Patent Number: 5,562,684
[45] Date of Patent: Oct. 8, 1996

[54] SURGICAL KNOT PUSHER DEVICE AND IMPROVED METHOD OF FORMING KNOTS

[75] Inventor: Gene W. Kammerer, East Brunswick, N.J.

[73] Assignee: Ethicon, Inc., Somerville, N.J.

[21] Appl. No.: 320,483

[22] Filed: Oct. 11, 1994

[51] Int. Cl.⁶ ............................................. A61B 17/04
[52] U.S. Cl. ................. 606/139; 606/144; 606/148; 289/17
[58] Field of Search ............................. 606/139, 144, 606/148; 289/2.5, 17

[56] References Cited

U.S. PATENT DOCUMENTS

| | | | |
|---|---|---|---|
| 4,961,741 | 10/1990 | Hayhurst | 606/148 |
| 5,041,129 | 8/1991 | Hayhurst et al. | 606/139 |
| 5,084,058 | 1/1992 | Li | 606/148 |
| 5,087,263 | 2/1992 | Li | 606/148 |
| 5,100,415 | 3/1992 | Hayhurst | 606/139 |
| 5,129,912 | 7/1992 | Noda et al. | 606/139 |
| 5,144,961 | 9/1992 | Chen et al. | 606/139 |
| 5,176,691 | 1/1993 | Pierce | 606/144 |
| 5,192,287 | 3/1993 | Fournier et al. | 606/139 |
| 5,201,744 | 4/1993 | Jones | 606/139 |
| 5,211,650 | 5/1993 | Noda | 606/139 |
| 5,217,471 | 6/1993 | Burkhart | 606/139 |
| 5,234,444 | 8/1993 | Christoudias | 606/139 |
| 5,234,445 | 8/1993 | Walker et al. | 606/139 |
| 5,281,238 | 1/1994 | Chin et al. | 606/139 |
| 5,282,809 | 2/1994 | Kammerer et al. | 606/148 |
| 5,284,485 | 2/1994 | Kammerer et al. | 606/139 |
| 5,292,327 | 3/1994 | Dodd et al. | 606/139 |
| 5,324,298 | 6/1994 | Phillips et al. | 606/148 |
| 5,334,200 | 8/1994 | Johnson | 606/139 |

FOREIGN PATENT DOCUMENTS 2247841  3/1992  United Kingdom .

*Primary Examiner*—Gary Jackson
*Attorney, Agent, or Firm*—Emil R. Skula; Charles Boukus, Jr.

[57] ABSTRACT

A surgical knot pusher device comprises a thick-walled cannula or tube having a beveled elliptical face and a central channel for slidably receiving one end of a suture. The other end of the suture is slidably inserted in one of a pair of longitudinal grooves formed on the outer surface of the cannula which intersect the elliptical face at the opposite ends of its major axis. One of the longitudinal grooves extends along the longest portion of the cannula and the other longitudinal groove extends along the shortest portion of the of the cannula. As the knot pusher device is inserted into a surgical port, a knot formed in the suture is engaged by the beveled face and advanced toward a surgical site. A notch is formed at the proximal end of the cannula for receiving the end of the suture threaded into the central channel. A threading element comprising an elongated rod with a deformable loop is provided to thread the suture into the central channel of the cannula.

13 Claims, 16 Drawing Sheets

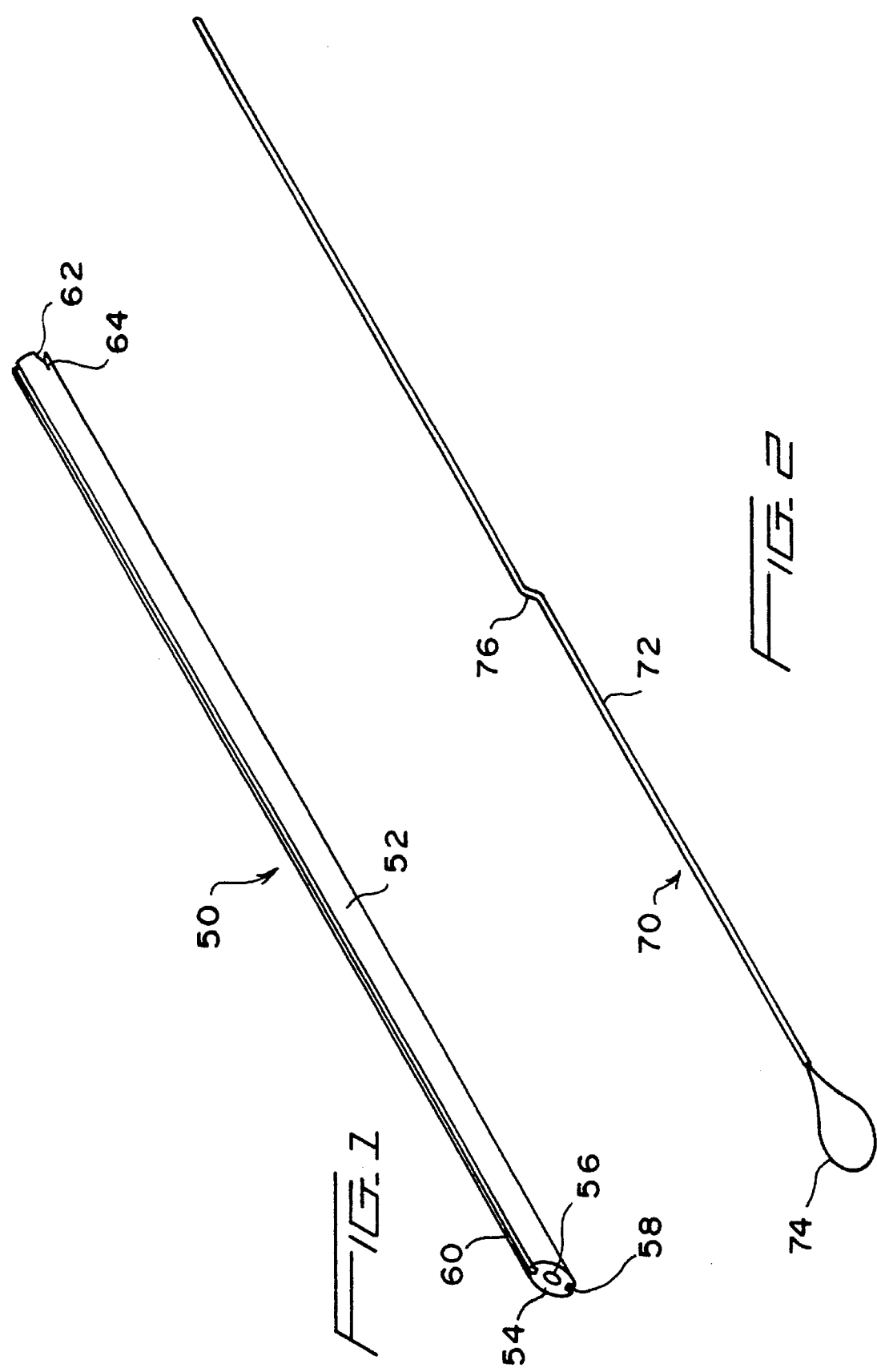

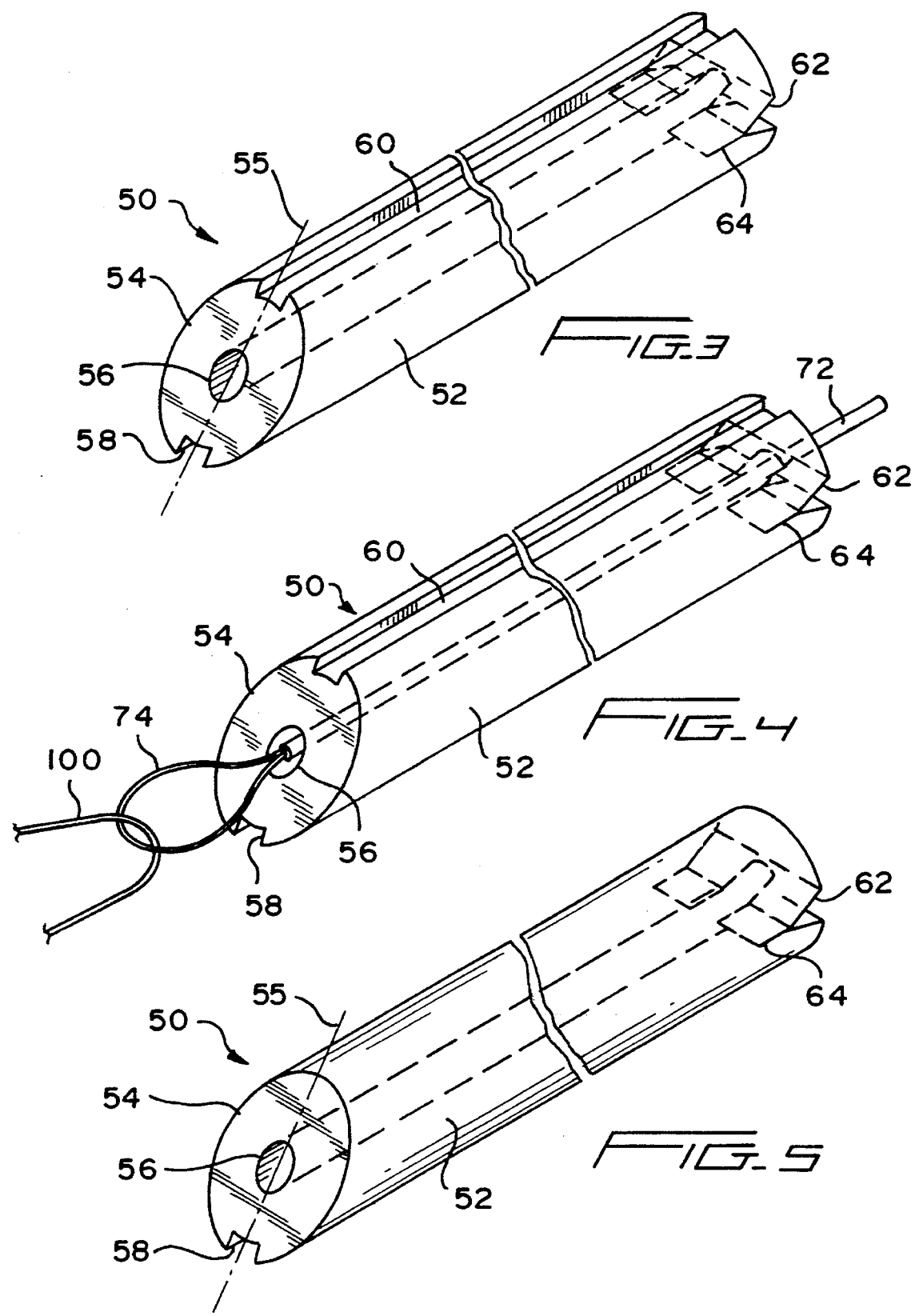

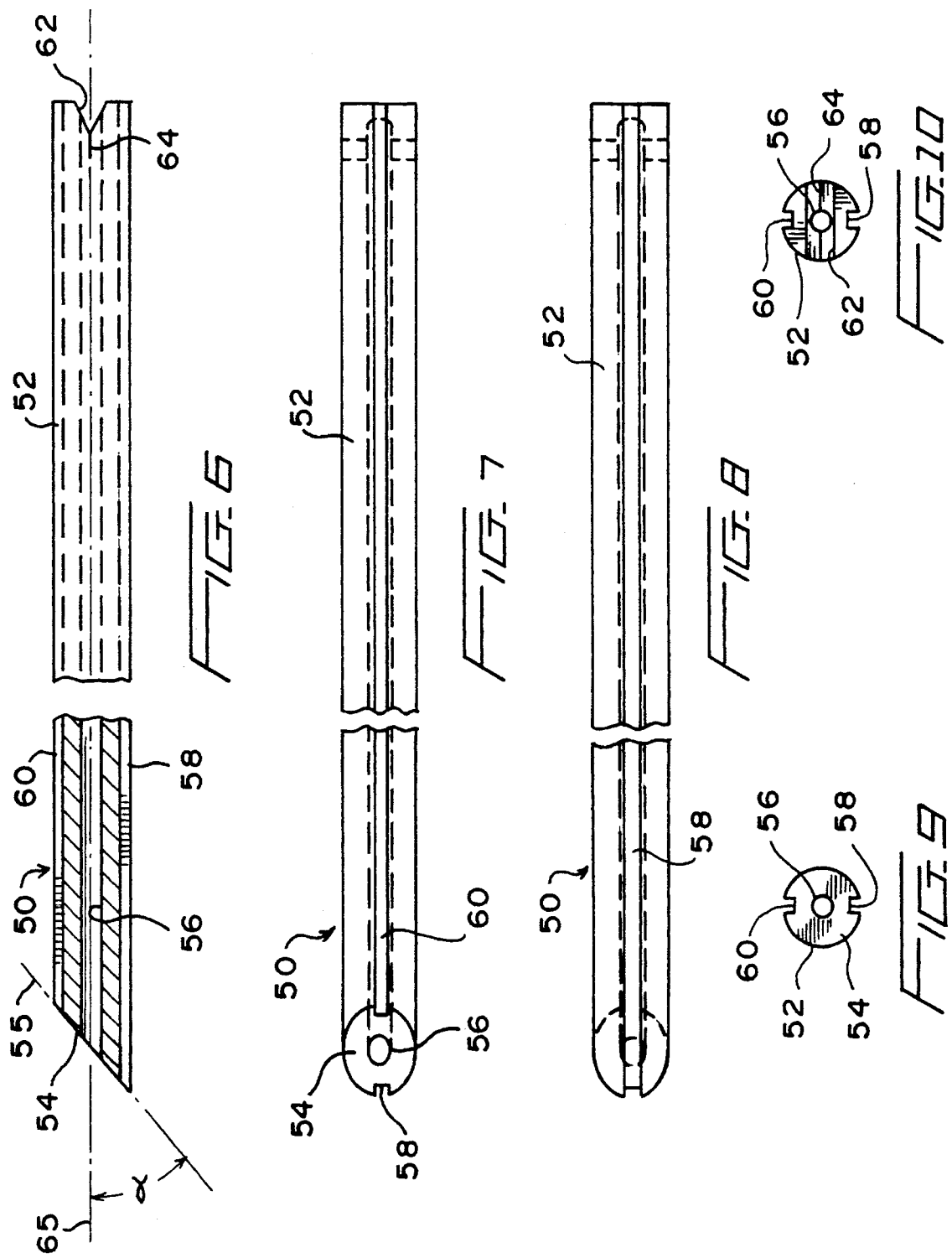

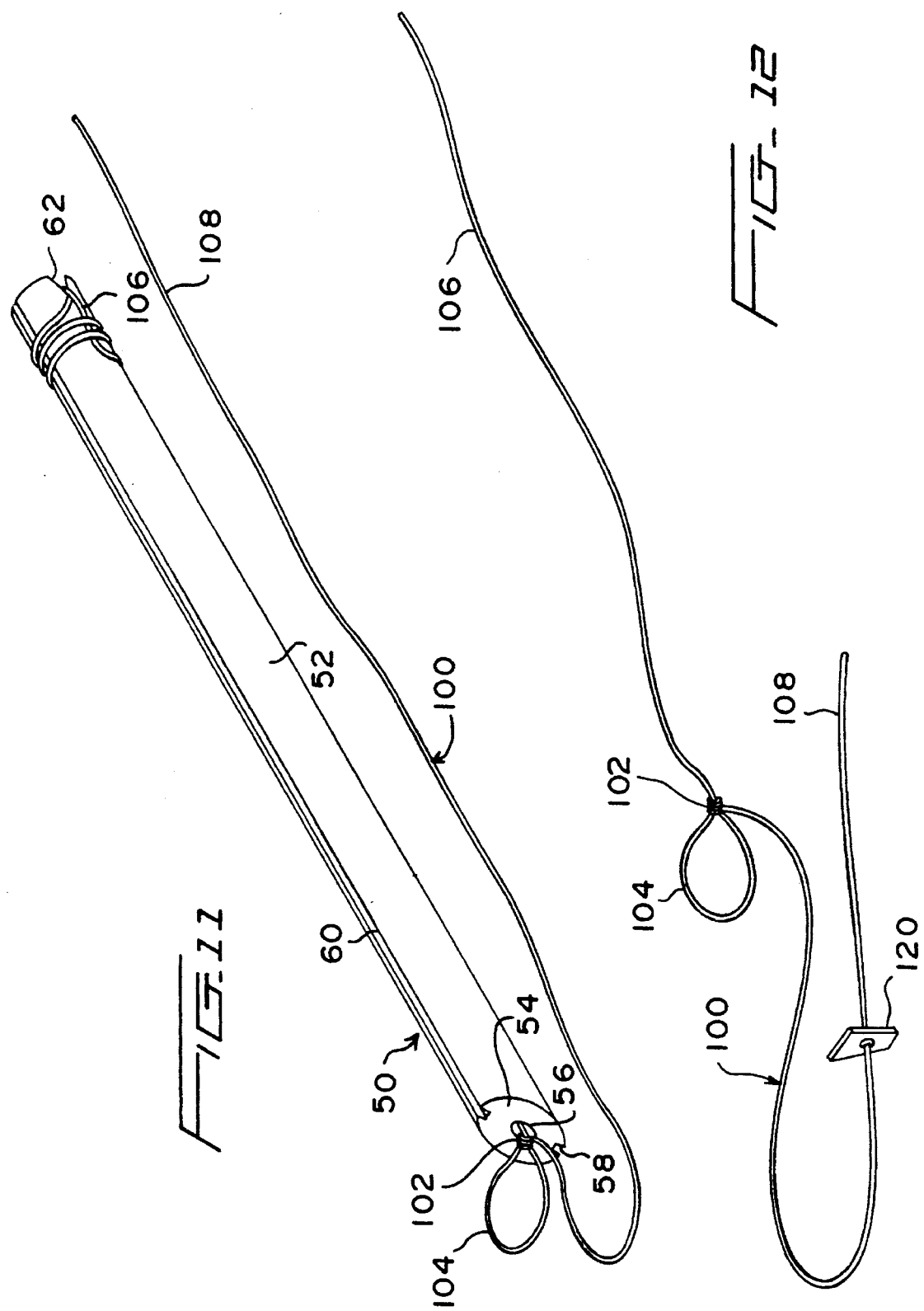

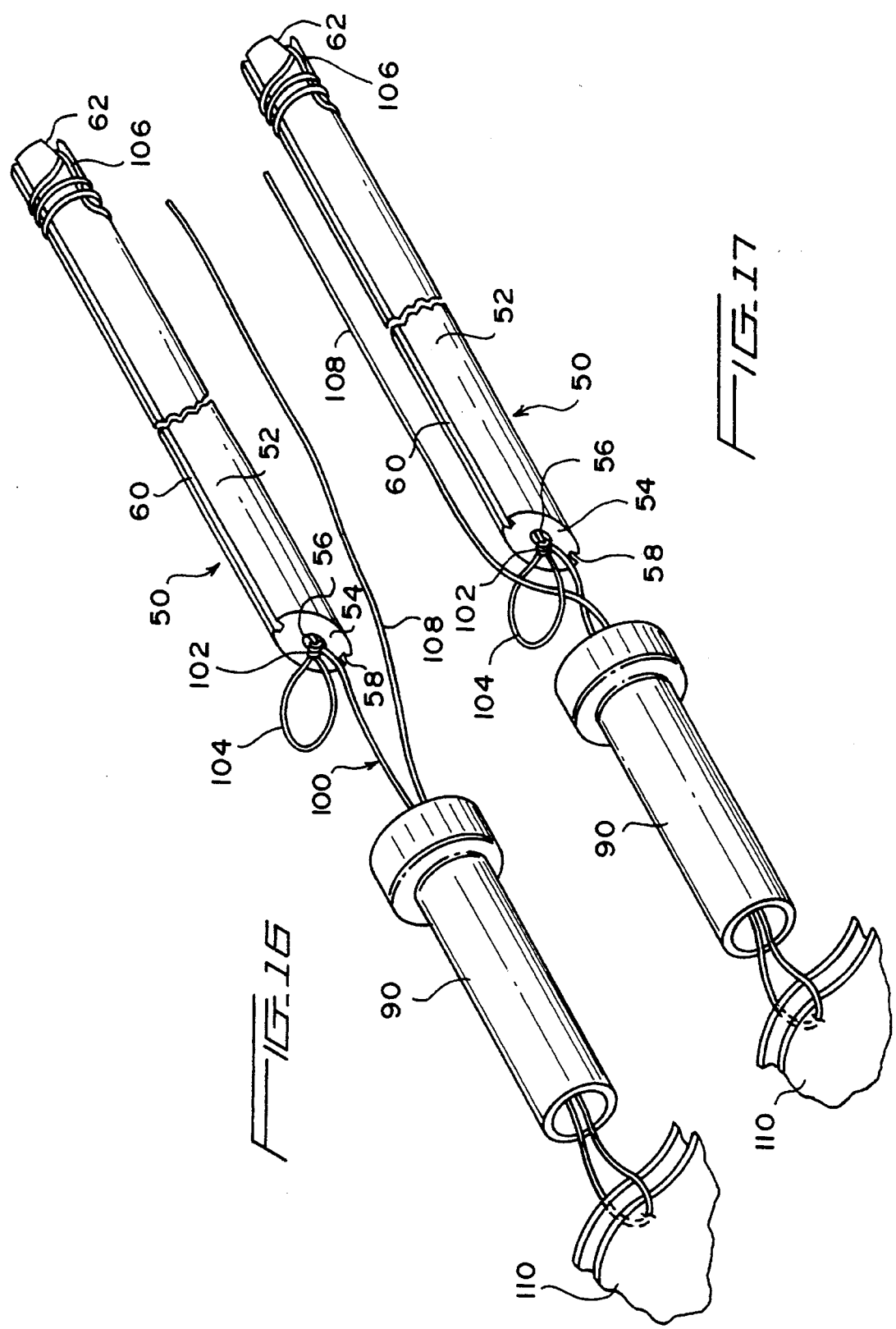

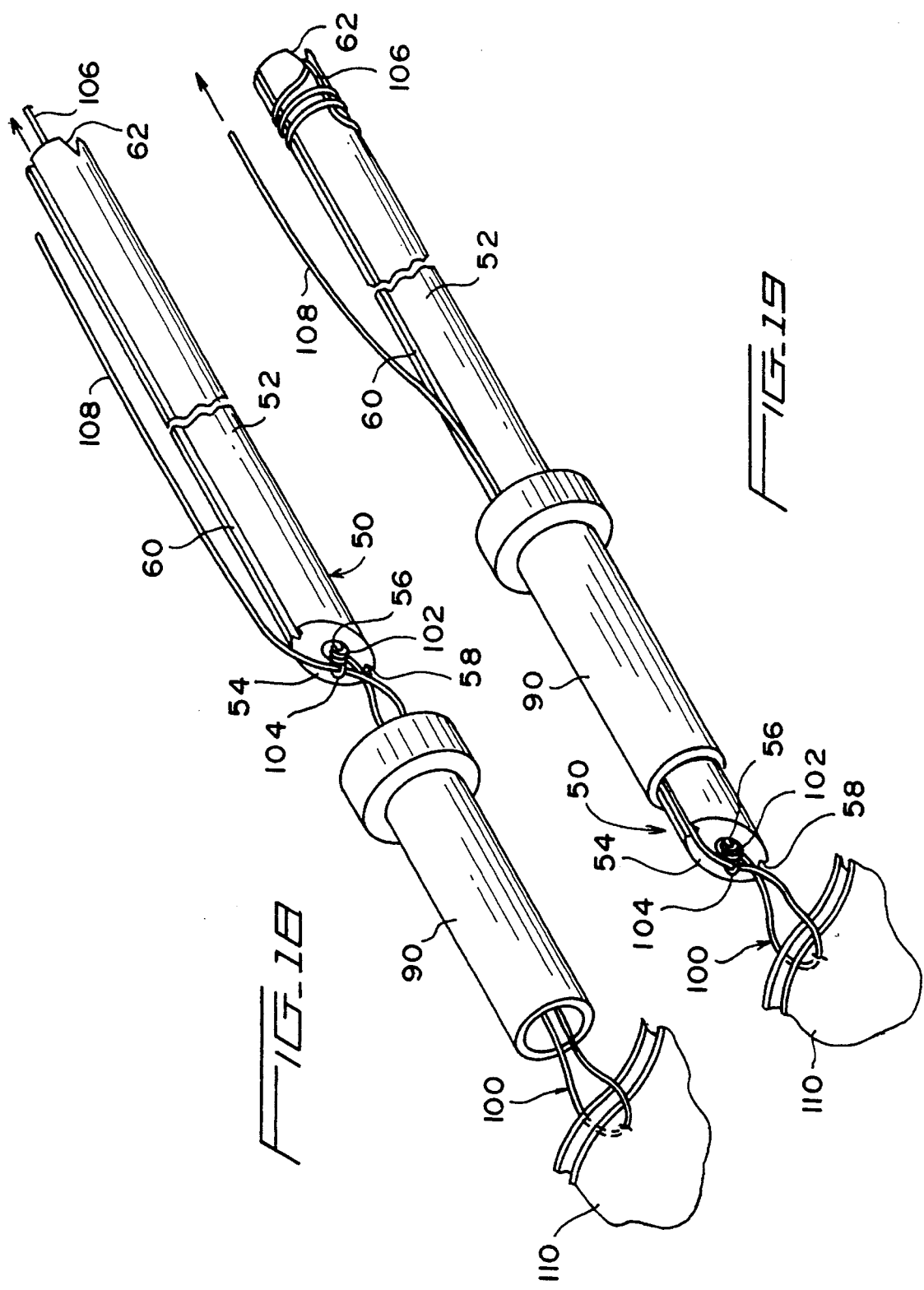

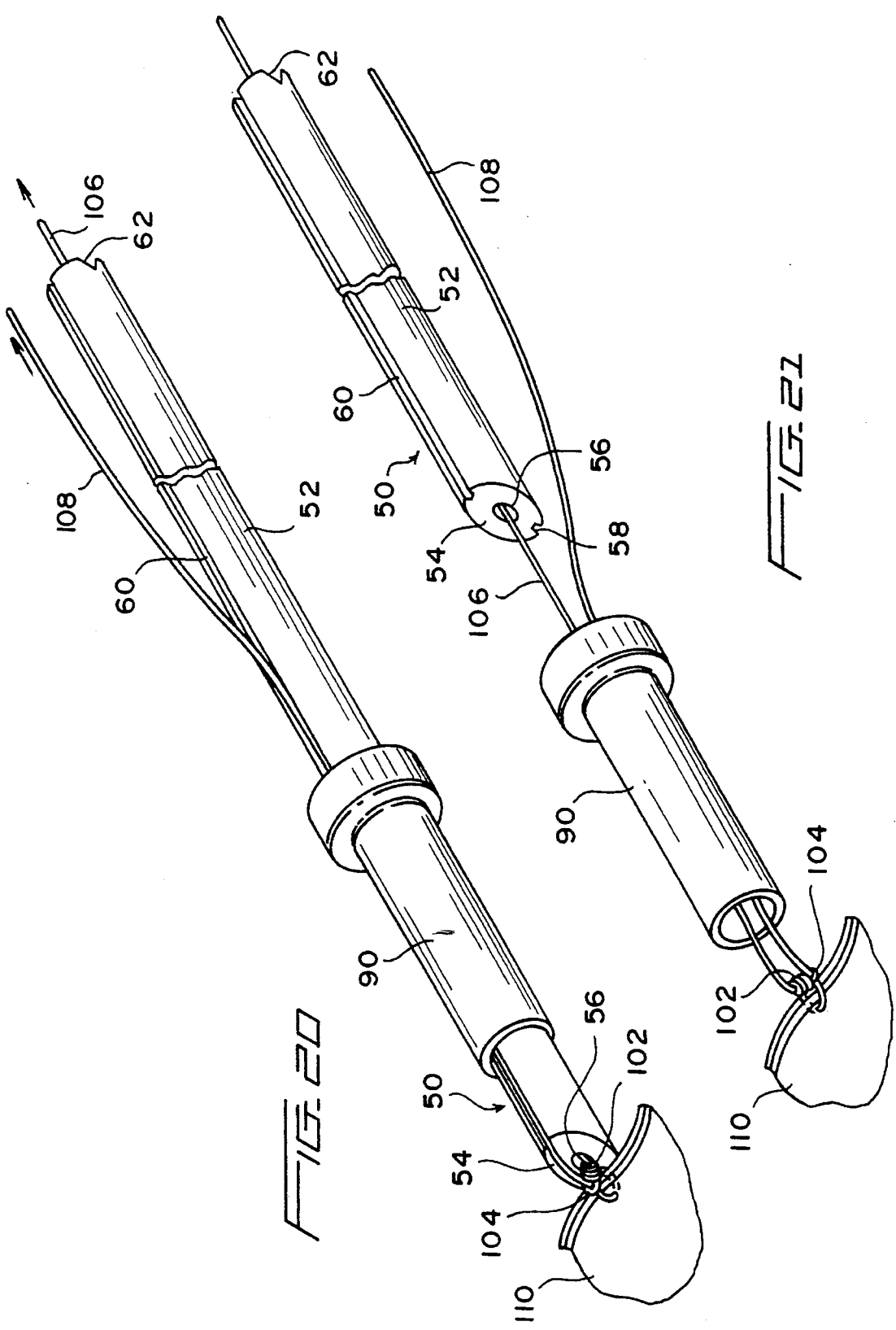

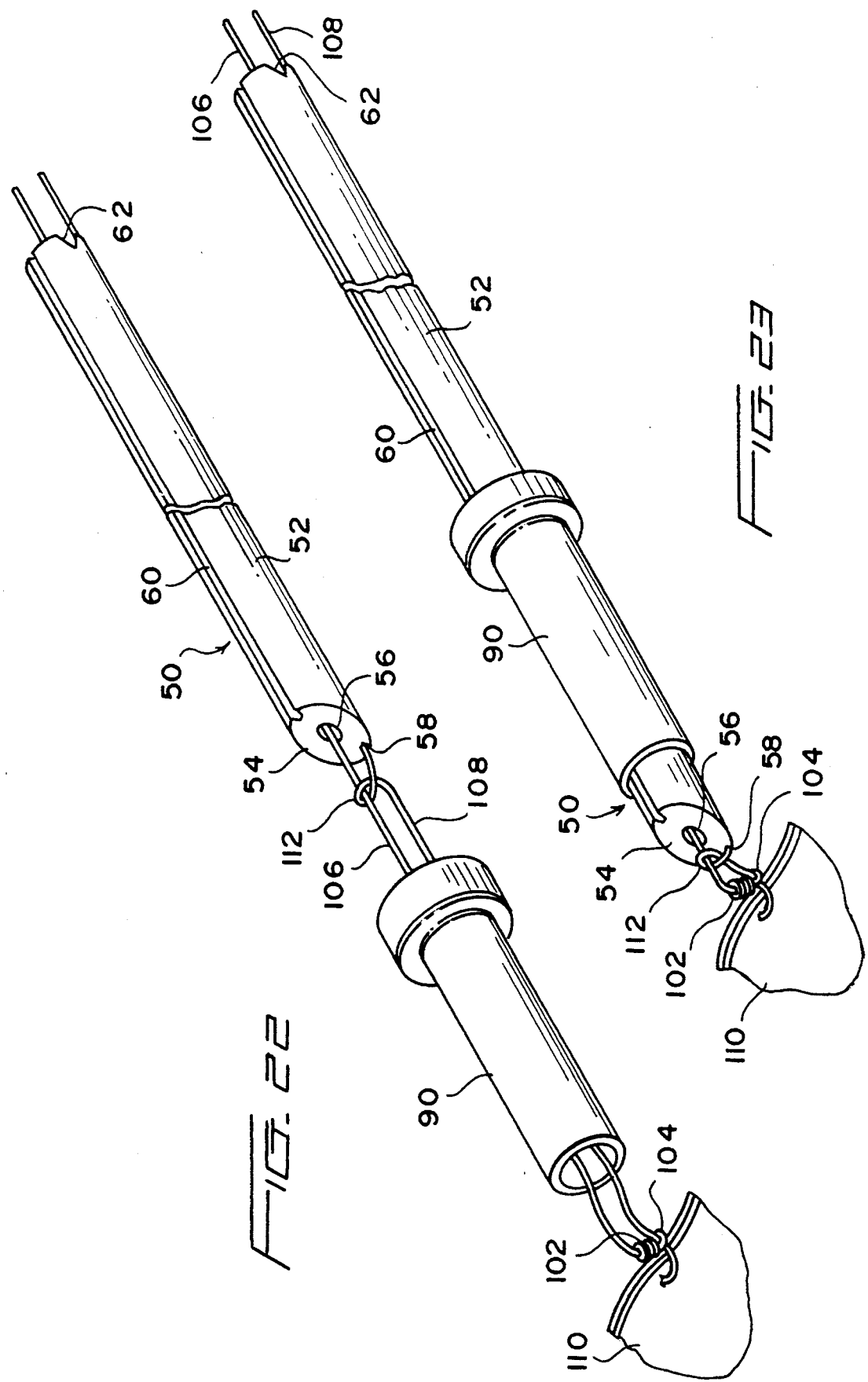

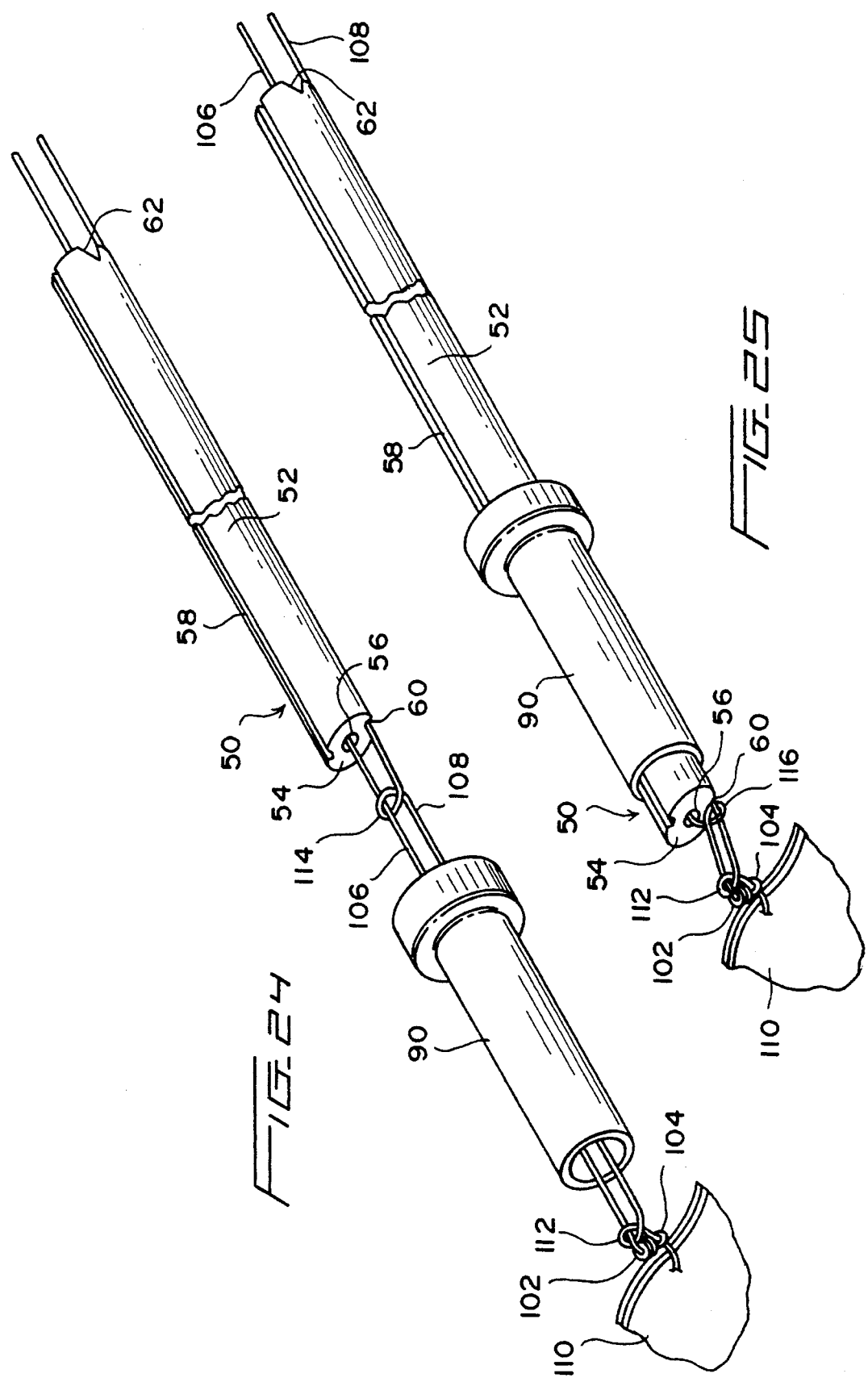

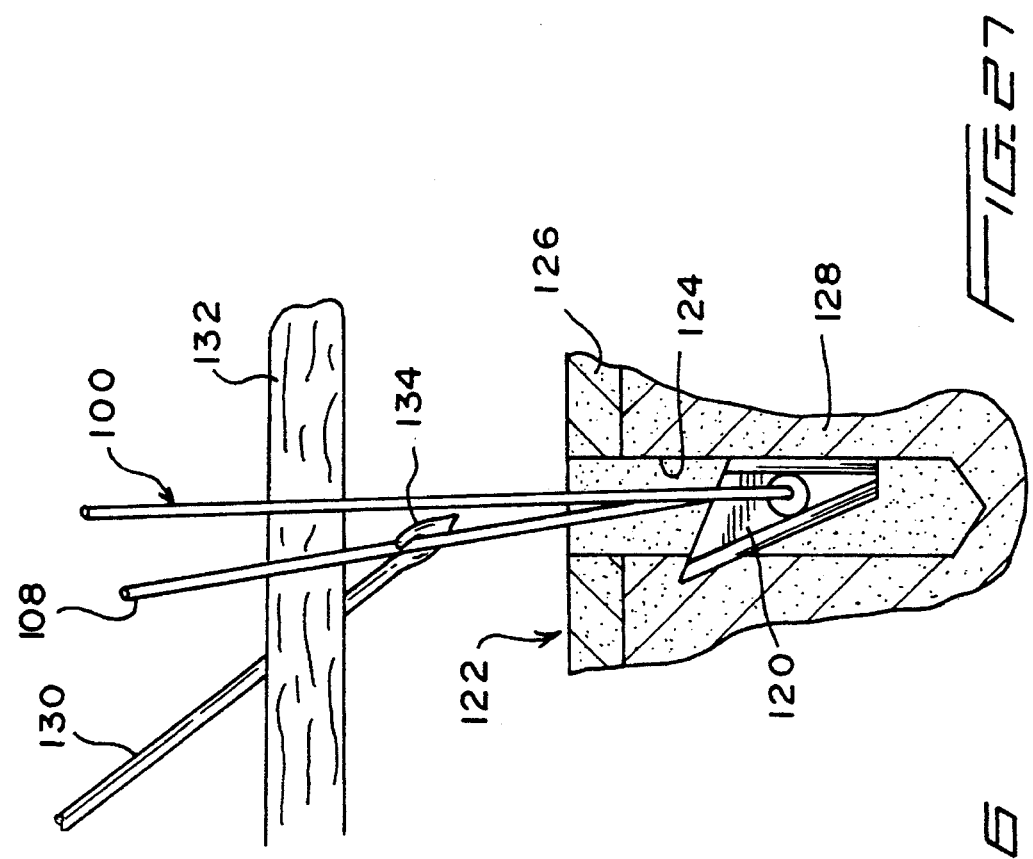
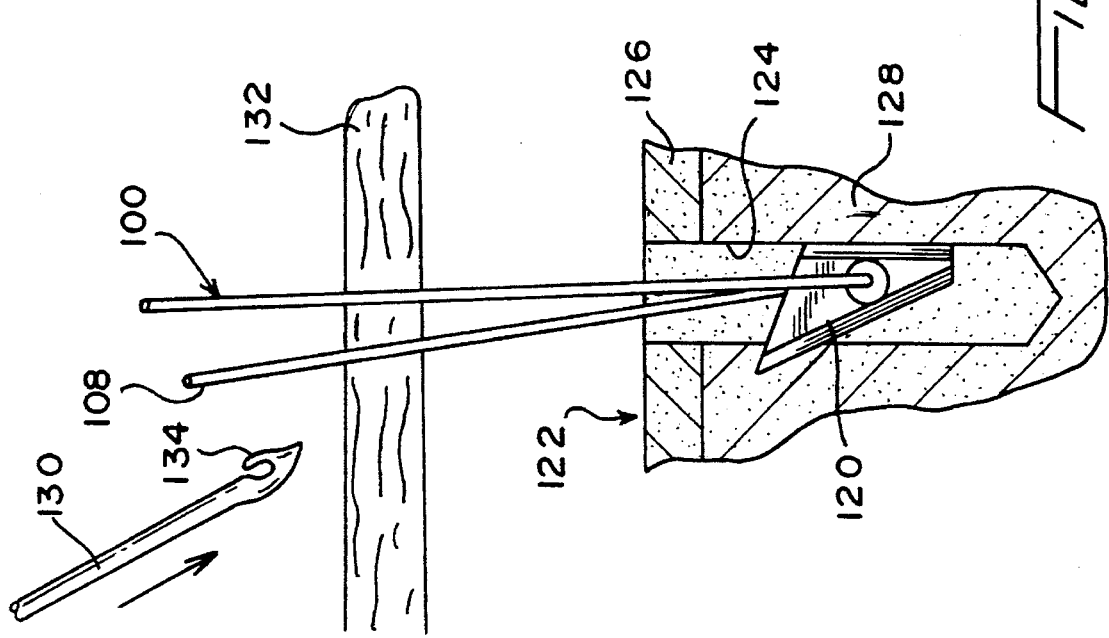

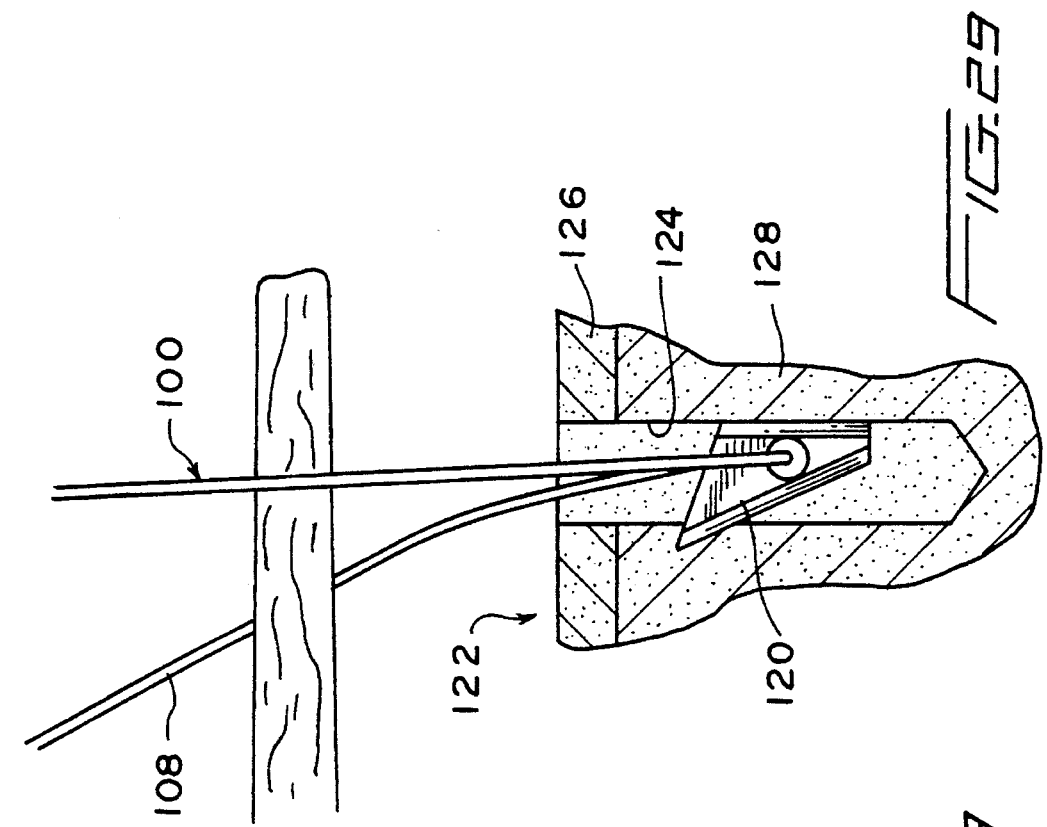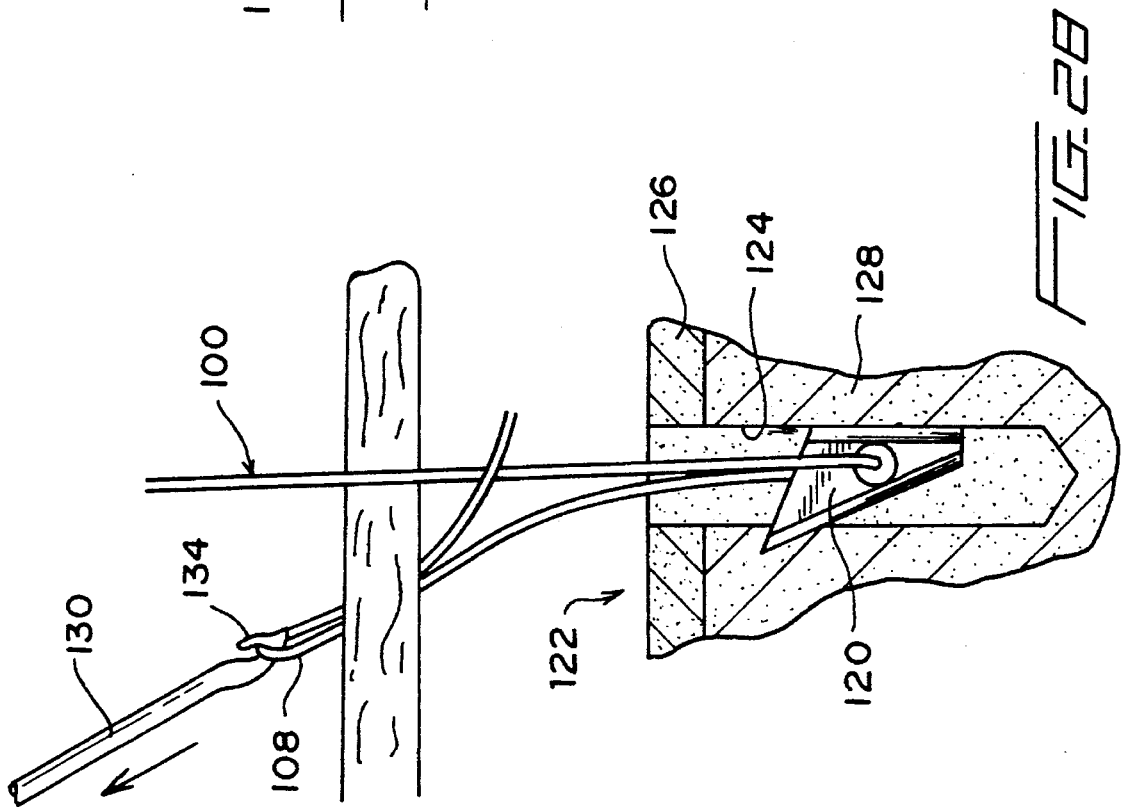

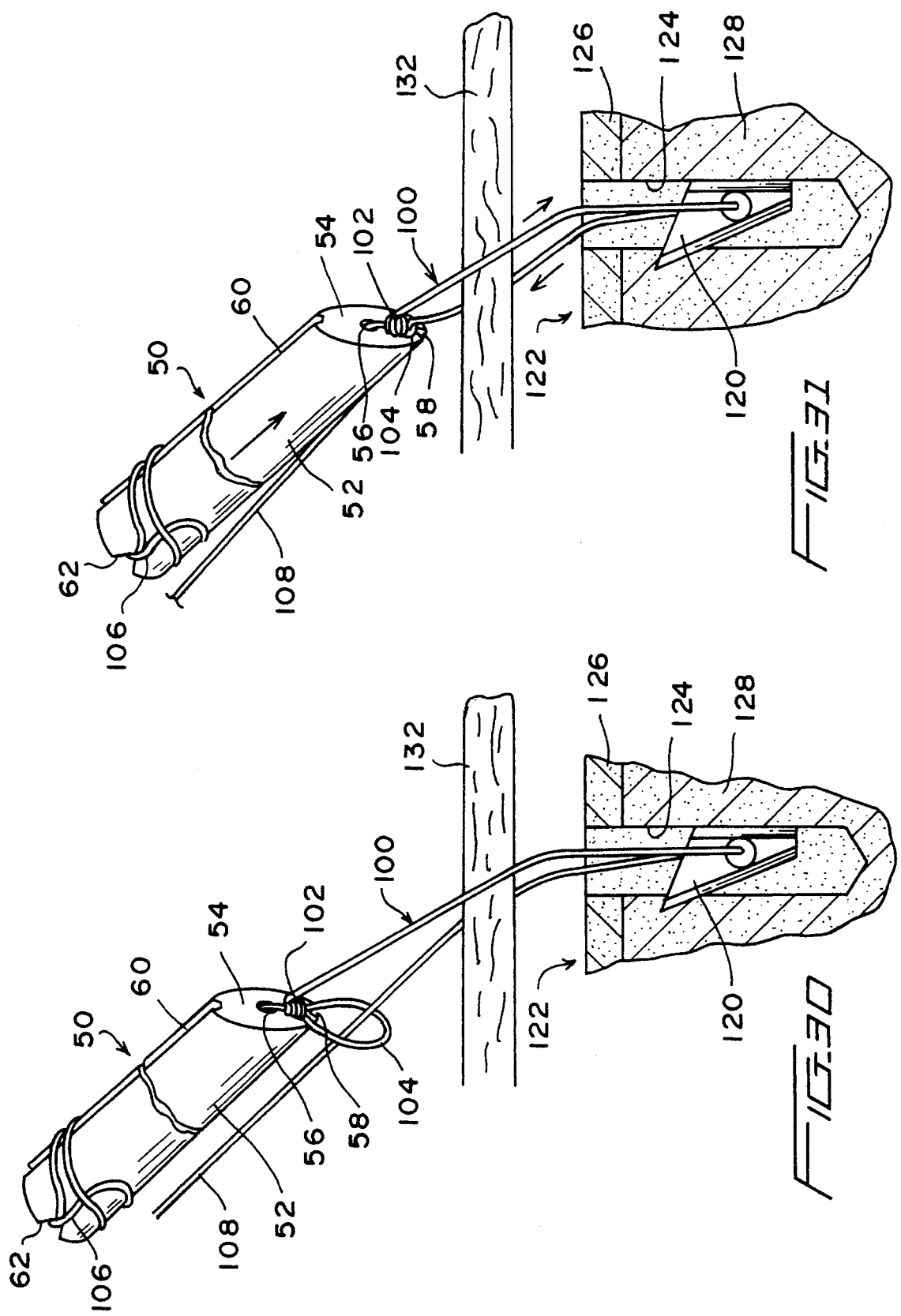

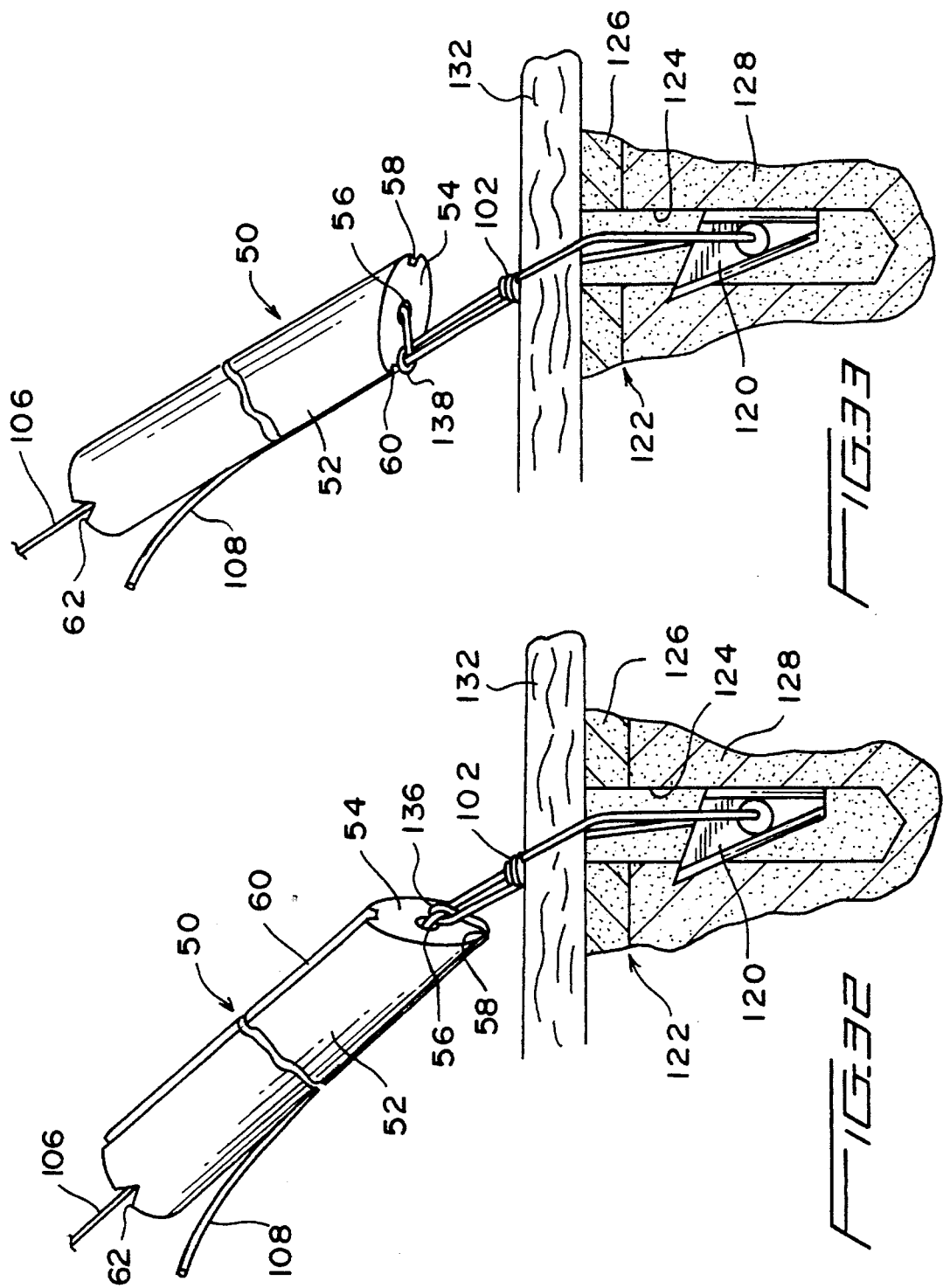

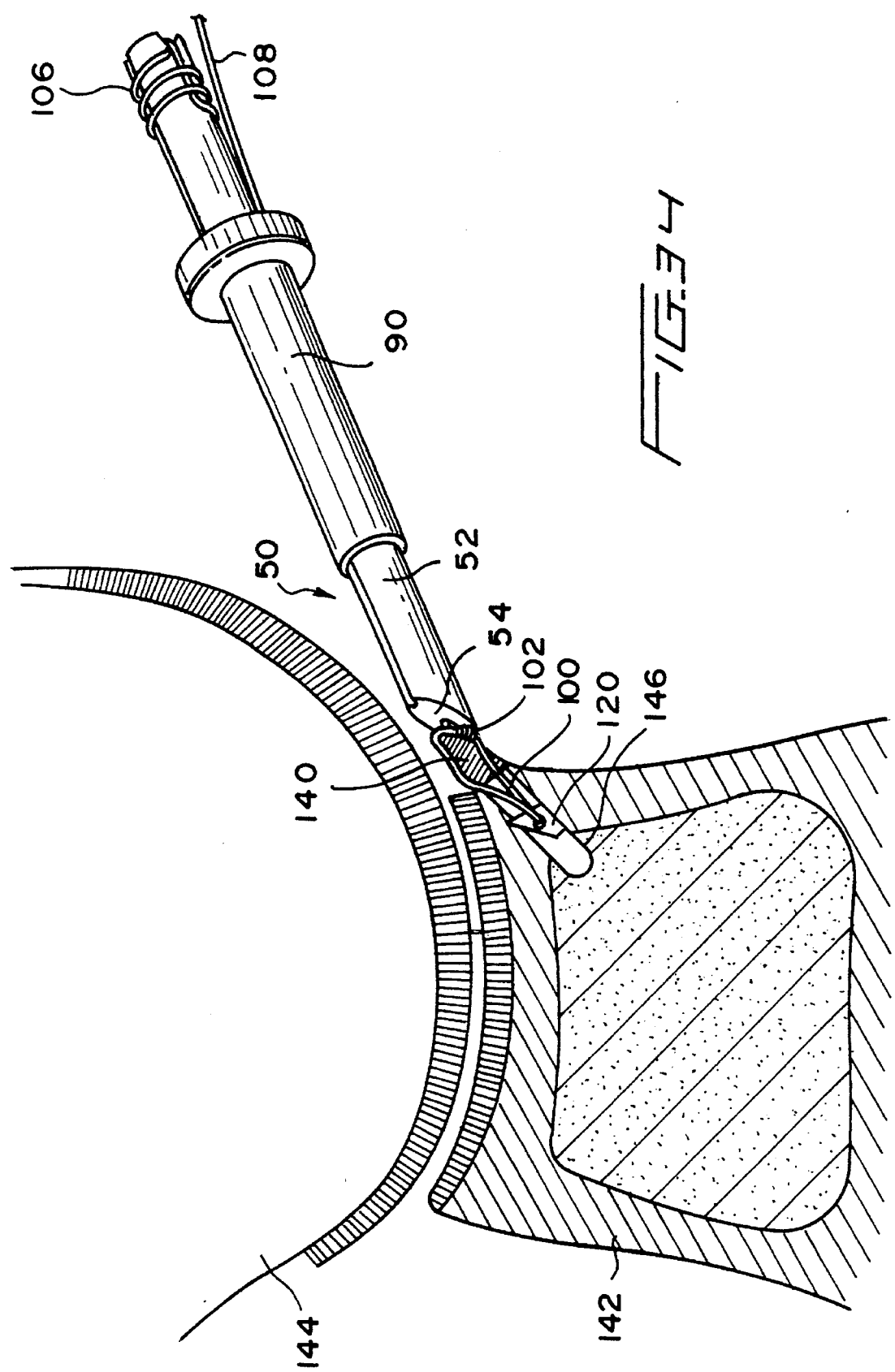

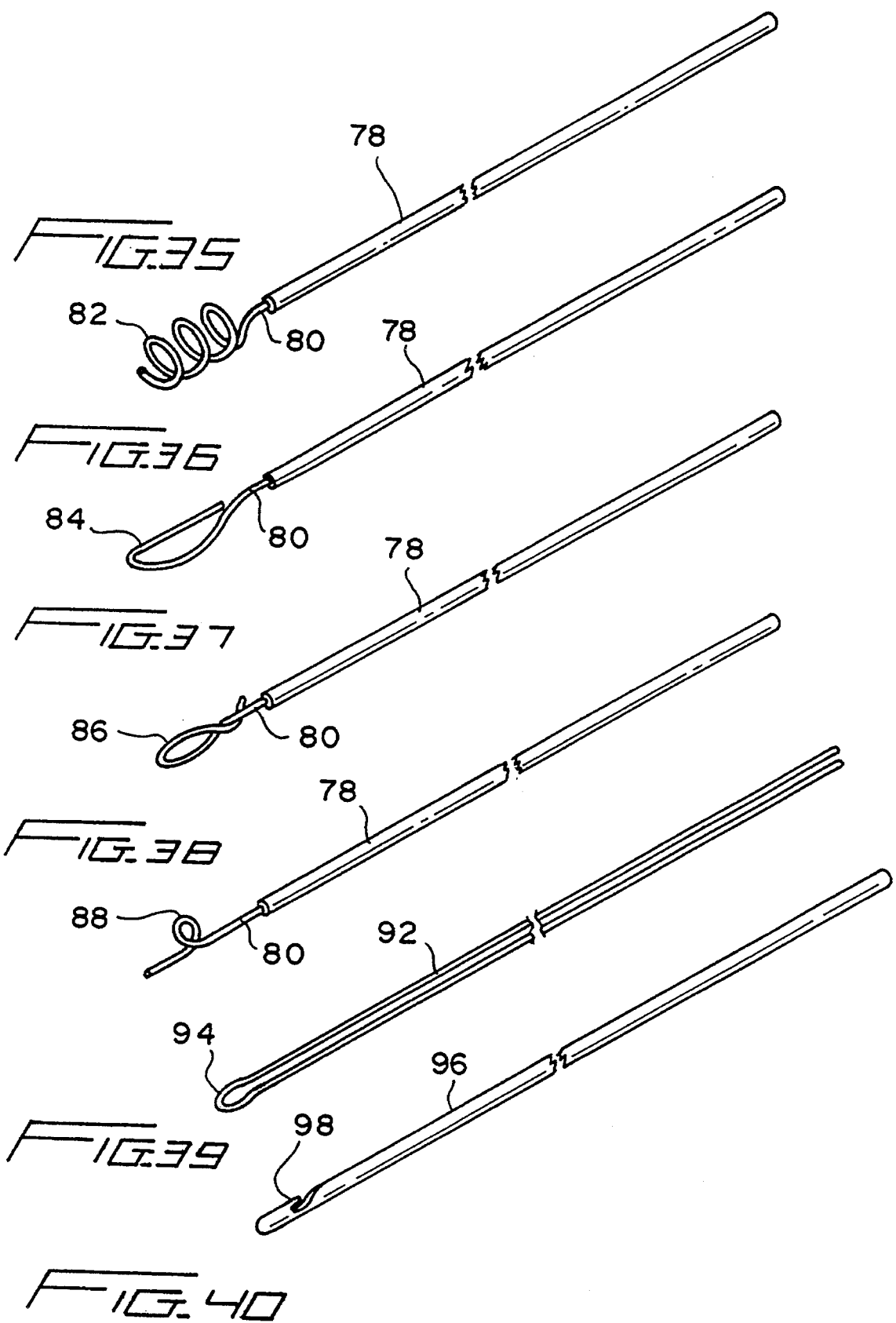

SURGICAL KNOT PUSHER DEVICE AND IMPROVED METHOD OF FORMING KNOTS

FIELD OF THE INVENTION

The present invention relates to a surgical knot pusher device and, more particularly, to a knot pusher device for advancing knots formed in a suture through a surgical port. The invention also relates to an improved method of forming knots in a suture at a surgical site inside the human body.

BACKGROUND OF THE INVENTION AND PRIOR ART

As medical and hospital costs continue to increase, surgeons are constantly striving to develop advanced surgical techniques. Advances in the surgical field are often related to the development of operative techniques which involve less invasive surgical procedures and reduce overall patient trauma. In this manner, length of hospital stays can be significantly reduced, and therefore the hospital and medical costs can be reduced as well.

One of the truly great advances in recent years to reduce the invasiveness of surgical procedures is endoscopic surgery. Endoscopic surgery involves the use of an endoscope, which is an instrument permitting the visual inspection and magnification of any cavity of the body. The endoscope is inserted through a tube, which is conventionally referred to as a cannula, after puncture of a hole into the soft tissue protecting the body cavity. The hole is made with a trocar, which is a sharp-pointed instrument. The trocar includes an obturator, or cutting implement, which is slidably and removably disposed within a trocar cannula. The obturator will puncture a hole in the tissue equal in size to the inner diameter of the trocar cannula. After puncture, the obturator can be slidably withdrawn from the trocar cannula. The surgeon can then perform diagnostic and therapeutic procedures at the surgical site with the aid of specialized instrumentation designed to fit through the trocar cannula and additional trocar cannulas providing openings into the desired body cavity as may be required.

In many surgical procedures, including those involving endoscopic surgery, it is often necessary to tie knots. For example, suturing to approximate tissue requires the formation of a suture knot for placement of a stitch. Additionally, ligating blood vessels to be cut within the surgical site is often necessary in numerous surgical procedures. The vessels may then be severed between the ligations. A primary reason for ligating the vessels is to maintain the surgical site free of an excess of blood and to reduce blood loss in the patient.

Conventionally, surgeons have closed blood vessels with ligatures, which are long, relatively straight strands of suture material. As is the case with the formation of a suture knot to place a stitch, the surgeon must manually tie a knot on the ligature after the ligature is looped around the vessel desired to be closed. Unfortunately, the formation of a knot on sutures and conventional ligatures is tedius and time-consuming during endoscopic surgical applications where the manual operative techniques of a surgeon within the surgical site are severely restricted.

In more recent years, endoscopic devices and techniques have been developed for forming and advancing knots through a surgical port to surgical sites inside the human body. Examples of such devices are disclosed in U.S. Pat. Nos. 5,144,961, 5,234,445, 5,282,809 and 5,284,485 assigned to Ethicon, Inc., the assignee of the present invention.

Chen et al U.S. Pat. No. 5,144,961 discloses an endoscopic ligating device comprising a surgical needle, a tube and a filamentary strand attached at its distal end to the surgical needle and slidably engaged at its proximal end about the tube with a partially tightened knot. The surgical needle and the filamentary strand are passed through a trocar, looped over a vessel to be ligated, and passed back up through the trocar outside the body. After the needle is removed, the filamentary strand is passed through the tube until a portion of the strand protrudes from the proximal end of the tube. The partially tightened knot is disengaged from the tube and tightened about the filamentary strand at the distal end of the tube. While maintaining a firm grip on the portion of the filamentary strand protruding from the proximal end of the tube, the tightened knot is advanced by pushing the knot along the filamentary strand with the distal portion of the tube.

Walker et al U.S. Pat. No. 5,234,445 discloses an endoscopic suturing device comprising a cannula including a beveled surface at its distal end, a first channel extending axially therethrough, and a second channel extending from the beveled surface to the first channel for receiving a suture provided with a slit, knot. The slide end of the suture is threaded through the first and second channels and protrudes from the proximal end of the cannula. A partial obstruction is provided in the axial channel to prevent the slide end of the suture from sliding back inside the cannula.

Kammerer et al U.S. Pat. No. 5,282,809 discloses an endoscopic suturing device comprising a cannula with a pair of channels for receiving first and second sutures. Each suture has a slide end, a distal loop, and a slip knot securing the distal loop to the slide end. One of the sutures has a stay end with an attached needle extending from the slip knot. The first and second channels in the cannula terminate at opposed beveled surfaces at the distal end of the cannula. The loops of the slip knots are used to form anchor knots for a row of stitches which close a wound.

Kammerer et al U.S. Pat. No. 5,284,485 discloses an endoscopic knotting device of the type disclosed in U.S. Pat. No. 5,144,961 including a surgical needle, a hollow tube, and a filamentary strand attached at its distal end to the surgical needle and slidably engaged at its proximal end about the tube with a partially tightened slip knot. The device includes a wire-like member extending through the hollow tube and provided with a deformable distal loop for threading the filamentary strand through the hollow tube when the surgical needle is detached from the strand.

Another type of a knot transfer instrument disclosed in Christoudias U.S. Pat. No. 5,234,444 comprises a cylindrical rod with two diametrically opposed driver grooves which accommodate the thread limbs of a knot to be delivered through a port into the abdominal cavity. The driver grooves terminate at a lower driver face adjacent to which the knot is formed. The instrument has converging grooves at its upper face which facilitate the sliding of the thread limbs therealong.

In another type of a knot pusher disclosed in U.S. Pat. No. 5,196,691 and U. K. Patent 2,247,841, an elongated rod is provided with a concave face for pushing a suture winding and a pair of opposed eyelets angled outwardly from the face for guiding and retaining the suture ends. In the use of knot pushers of this type, there is a tendency for the strands of the suture to twist together as the knot pusher is advanced toward the surgical site.

SUMMARY OF THE INVENTION

The present invention provides an improved surgical knot pusher device which facilitates the formation and advancement of knots in sutures to surgical sites inside the body where access is restricted. The knot pusher device enables both slip knots and additional throws, e.g., half-hitch knots, to be advanced to surgical sites inside the body, through either a surgical port in endoscopic surgery or an incision in open surgery. The knot pusher device facilitates the formation of surgical knots with enhanced strength and resistance to slippage by alternating the post and loop ends in the tying of the knots in the sutures.

In accordance with the present invention, a surgical knot pusher device for advancing knots formed in a suture comprises a cannula having a beveled face at its distal end for engaging a knot formed by the ends of one or more sutures and a channel extending axially therethrough for receiving one suture end, and a longitudinal groove formed on an outer surface of the cannula and intersecting the periphery of the beveled face for receiving another suture end. Preferably, the beveled face of the cannula has an elliptical configuration. The longitudinal groove on the outer surface of the cannula intersects the periphery of the elliptical face at one end of its major axis.

In the surgical knot pusher device of this invention, the arrangement of the beveled face, the central channel and the longitudinal groove on the cannula enables the configuration of the completed knot to be precisely controlled. Preferably, the longitudinal groove extends along the longest portion of the outer surface of the cannula. The suture end received in the central channel becomes the post end of the knot and the other suture end received in the longitudinal groove along the longest portion of the cannula becomes the loop end of the knot when the knot is engaged by the beveled face of the cannula. Alternately, the longitudinal groove extends along the shortest portion of the outer surface of the cannula. The suture end received in the central channel becomes the loop end of the knot and the other suture end received in the longitudinal groove on the shortest portion of the cannula becomes the post end of the knot when the knot is engaged by the beveled face of the cannula.

A preferred embodiment of the surgical knot pusher device comprises a cannula having a beveled face at its distal end for engaging a knot formed by the ends of one or more sutures and a channel extending axially therethrough and terminating at the beveled face for slidably receiving one suture end, and a pair of longitudinal grooves formed on an outer surface of the cannula, with each of the grooves intersecting the periphery of the beveled face for slidably receiving another suture end. Preferably, the beveled face of the cannula has an elliptical configuration. The longitudinal grooves on the cannula intersect the periphery of the elliptical face at the opposite ends of its major axis.

In the preferred embodiment of the surgical knot pusher device, one of the longitudinal grooves extends along the longest portion of the outer surface of the cannula and the other longitudinal groove extends along the shortest portion of the outer surface of the cannula. The suture end received in the central channel becomes the post end of the knot and the other suture end received in the longitudinal groove along the longest portion of the cannula becomes the loop end of the knot when the knot is engaged by the beveled surface of the cannula. Alternately, the suture end received in the central channel becomes the loop end of the knot and the other suture end received in the longitudinal groove along the shortest portion of the cannula becomes the post end of the knot when the knot is engaged by the beveled face of the cannula.

Another aspect of the invention relates to improved methods of forming knots in a suture attached to internal body tissue at a surgical site inside a body. The methods can be performed by using the knot pusher device of this invention. The methods can be employed to advance and tighten a pre-formed slip knot in a suture and to form additional knots or throws in the suture at the surgical site inside the body.

BRIEF DESCRIPTION OF THE DRAWINGS

The foregoing and other objects, aspects and advantages will be better understood from the following detailed description of the preferred embodiments of the invention with reference to the drawings, in which:

FIG. 1 is perspective view of a first embodiment of a knot pusher device constructed in accordance with this invention;

FIG. 2 is a perspective view of a threading element which is fused to thread a suture into the knot pusher device of FIG. 1;

FIG. 3 is an enlarged perspective view showing a beveled face at the distal end of the knot pusher device of FIG. 1;

FIG. 4 is an enlarged perspective view of the threading element of FIG. 2 inserted into the distal end of the knot pusher device;

FIG. 5 is an enlarged perspective view of a second embodiment of the knot pusher device of this invention;

FIG. 6 is an enlarged, partially cutaway side view of the knot pusher device of FIG. 1;

FIG. 7 is a top view of the knot pusher device of FIG. 6;

FIG. 8 is a bottom view of the knot pusher device of FIG. 6;

FIG. 9 is a front view of the knot pusher device of FIG. 6;

FIG. 10 is a rear view of the knot pusher device of FIG. 6;

FIG. 11 is a perspective view of the knot pusher device of FIG. 1 assembled with a suture including a pre-tied slip knot;

FIG. 12 is a perspective view of the suture of FIG. 11 attached to a suture anchor;

FIGS. 16–20 illustrate the use of the knot pusher device of FIG. 11 to advance and tighten the slip knot in the suture;

FIGS. 21–25 illustrate the use of the knot pusher device of FIG. 11 to form additional knots behind the tightened slip knot;

FIGS. 26–29 illustrate the use of the suture and anchor of FIG. 12 to re-attach a ligament to a bone;

FIGS. 30–33 illustrate the use of the knot pusher device of FIG. 11 to form a surgical knot to secure the ligament to the bone;

FIG. 34 illustrates the use of the knot pusher device of FIG. 11 to place a surgical knot in arthroscopic surgery on a shoulder joint; and FIGS. 35–40 illustrate alternate embodiments of the suture threading element of the knot pusher device.

DETAILED DESCRIPTION OF PREFERRED EMBODIMENTS

Figure 13:
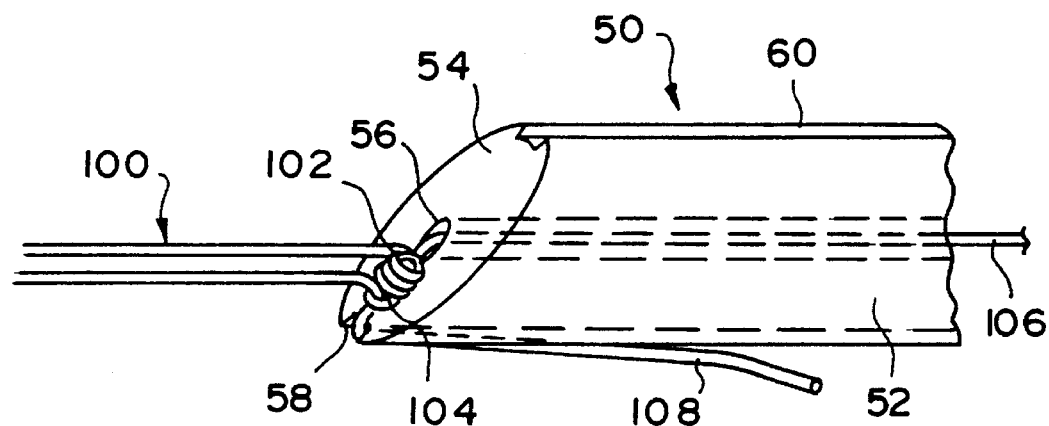
FIG. 13 is an enlarged perspective view of a slip knot in the suture engaged by the distal end of the knot pusher device of FIG. 11.

Referring to FIG. 1, the present invention is embodied in a surgical knot pusher device, generally 50, which is particularly suitable for use in arthroscopic surgery on shoulders, knees and other joints of the human body. However, it will be understood by persons skilled in the art that the knot pusher device 50 can be used in any type of endoscopic or open surgery to form and advance knots in a suture or ligature at a surgical site inside the human body where access is restricted.

As shown in FIGS. 6–8, the knot pusher device 50 comprises an elongated cannula 52 having a beveled face 54 at its distal end and a central channel 56 extending axially therethrough and terminating at the beveled face 54. The cannula 52 has a first longitudinal groove 58 formed on its outer surface and intersecting the periphery of the beveled face 54. In addition, the cannula 52 has a second longitudinal groove 60 formed on its outer surface and intersecting the periphery of the beveled face 54. The longitudinal grooves 58 and 60 are formed on opposite sides, e.g., top and bottom, of the cannula 52 (FIGS. 9–10).

As shown in FIG. 3, the cannula 52 has a circular cross section and the beveled face 54 has an elliptical configuration. The longitudinal grooves 58 and 60 intersect the periphery of the elliptical face 54 at the opposite ends of its major axis 55. The first longitudinal groove 58 extends along the longest portion of the outer cylindrical surface of the cannula 52. The second longitudinal groove 60 extends along the shortest portion of the outer cylindrical surface of the cannula 52.

The cannula 52 is a thick-walled tube having an outside diameter which is small enough to fit through a standard arthroscopic port having an inside diameter of about 7 mm (0.275 inches). The central channel 56 has an inside diameter which is large enough to slidably receive a suture used in arthroscopic surgery. The cannula 52 is long enough to enable the surgeon to hold and maneuver the cannula 52 from outside the body while its distal beveled end 54 is against the tissue to be sutured inside the body. Generally, the cannula 52 has a length of 8 to 10 inches or longer. However, the knot pusher device 50 is not limited to the above sizes and can be made larger or smaller for other applications.

Referring to FIGS. 6–8, the longitudinal grooves 58 and 60 on the outer cylindrical surface of the cannula 52 are aligned parallel to the central channel 56 along the longitudinal axis of the cannula 52. The longitudinal groove 58 extends along the full length of the bottom portion of the cannula 52. The longitudinal groove 60 extends along the full length of the top portion of the cannula 52. Each of the grooves 58 and 60 is sufficiently wide and deep to slidably receive a suture. For example, each of the grooves 58 and 60 has a width of 0.04 inch and a depth of 0.03 inch for receiving a conventional suture used in arthroscopic surgery.

Referring to FIG. 6, the elliptical face 54 at the distal end of the cannula 52 is beveled or slanted at an angle $\alpha$ in the range of 15° to 75° relative to the longitudinal axis 65 of the cannula 52. Preferably, the elliptical face 54 is beveled or slanted at an angle $\alpha$ of about 40° relative to the longitudinal axis 65 to facilitate the sliding and placement of knots formed in a suture.

As shown in FIG. 5, in an alternative embodiment of the knot pusher device 50, only one longitudinal groove 58 is formed on the outer cylindrical surface of the cannula 52. The longitudinal groove 58 terminates at the beveled face 54 and intersects the major axis 55 of the flat elliptical surface of the beveled face 54. Preferably, the longitudinal groove 58 extends along the longest portion of the outer cylindrical surface of the cannula 52. Alternatively, the longitudinal groove 58 can be formed along the shortest portion of the outer cylindrical surface of the cannula 52.

Referring to FIG. 5, the knot pushing characteristics of the knot pusher device 50 are optimized when the intersection of the longitudinal groove 58 with the major axis 55 of the elliptical face 54 is located on the longest portion of the cannula 52. If the intersection is moved to either side of the major axis 55, the ability of the device 50 to push knots is diminished. As the intersection is moved away from the end of the major axis 55 on the longest portion of the cannula 52, it becomes more difficult to achieve consistent reproducible knots which are easily pushed through a surgical port. As the intersection approaches the opposite end of the major axis 55 on the shortest portion of the cannula 52, the knot pushing ability of the device 50 is increased. However, when the longitudinal groove 58 is located along the shortest portion of the cannula 52 and intersects the opposite end of the major axis 55, the knot pushing capability is not as controllable in comparison with the longitudinal groove 58 intersecting the opposite end of the major axis 55 along the longest portion of the cannula 52.

Referring to FIGS. 3 and 6, anchor means in the form of a V-shaped notch 62 is provided at the proximal end of the cannula 52. The V-shaped notch 62 extends diametrically across the proximal end of the cannula 52 in a transverse direction. A narrow longitudinal slit 64 extends forwardly from the front end of the V-shaped notch 62. The slit 64 extends completely across the cannula 52. For example, the V-shaped notch 62 is tapered at an angle of 35°, i.e., 17½ on either side of the longitudinal axis 65 of the cannula 52. The length of the V-shaped notch 62 is approximately ⅛ inch. The total length of the V-shaped notch 62 and the slit 64 is approximately 3/16 inch or more.

The cannula 52 can be made of a conventional medical grade material, e.g., nylon, polypropylene, polycarbonate, stainless steel or teflon. The preferred embodiment of the cannula 52 consists of a stiff plastic material such as polypropylene.

Referring to FIG. 2, a suture threading element, generally 70, is provided for threading a suture through the central channel 56 of the cannula 52. The threading element 70 comprises a thin elongated rod 72 provided with a deformable wire loop 74 at its distal end. Preferably, the rod 72 is made of metal, e.g., stainless steel or spring steel, and the deformable loop 74 is made of a shape memory alloy, e.g., nitinol, which returns to its original shape after it is deformed. The loop 74 can also be made of other metals, e.g., stainless steel or spring steel. Alternatively, the rod 72 and the loop 74 can be made of plastic material, e.g., polypropylene.

As shown in FIG. 4, to thread a suture 100 into the central channel 56 of the cannula 52, the rod 72 is inserted into the central channel 56 with the loop 74 protruding from the distal end of the cannula 52. The suture 100 is inserted into the loop 74 and the rod 72 is pulled in the proximal direction through the cannula 52 to thread the suture 100 through the central channel 56. After the rod 72 is pulled through the cannula 52, the loop 74 expands to its original open shape and can be re-used to thread another suture into the cannula 52. The rod 72 can be straight or formed with an offset or bent portion 76 (FIG. 2) to provide a frictional fit inside the central channel 56 to hold the threading element 70 in place within the cannula 52.

In FIGS. 35–38, alternate embodiments of the suture threading element are shown for threading a suture into the knot pusher device 50 of this invention. Each of the suture threading elements comprises an elongated rod 78 provided with a wire 80 extending from its distal end which is shaped to capture the suture. The suture threading element is pulled through the central channel 56 (FIG. 11) to thread the suture into the cannula 52.

In the suture threading element of FIG. 35, the wire 80 extending from the distal end of the rod 78 is shaped into a helical coil 82 for capturing the suture. FIG. 36 shows a suture threading element in which the wire 80 at the distal end of the rod 78 is shaped as an elongated loop or hook 84 for capturing the suture.

In the suture threading element of FIG. 37, the wire 80 at the distal end of the rod 78 is twisted about itself to provide an elongated loop 86 for capturing the suture. FIG. 38 shows a suture threading element in which the wire 80 at the distal end of the rod 78 is looped to provide a eyelet 88 for capturing the suture.

Preferably, in each of the embodiments of FIGS. 35–38, the rod 78 is made of metal, e.g., stainless steel or spring steel. The wire 80 is made of a shape memory alloy, e.g., nitinol, which deforms when the suture threading element is pulled into the central channel 56 of the cannula 52 and returns to its original shape when the suture threading element is removed from the cannula 52. The wire 80 can also be made of other metals, e.g., stainless steel or spring steel. Alternatively, the rod 78 and the wire 80 can be made of plastic material, e.g., polypropylene.

As shown in FIG. 39, another embodiment of the suture threading element comprises a thin elongated wire 92 which is folded back upon itself to form a loop 94 at its distal end for capturing the suture to be threaded into the central channel 56 of the cannula 52. The wire 92 is preferably made of metal, e.g., a shape memory alloy, e.g., nitinol. The wire 92 can also be made of other metals, e.g., stainless steel or spring steel, or pastic material, e.g., polypropylene.

In the suture threading element of FIG. 40, an elongated rod 96 is notched adjacent to its distal end to provide a hook 98 for capturing the suture. The rod 96 is preferably made of metal, e.g., stainless steel or spring steel, or a plastic material, e.g. polypropylene.

Referring to FIG. 11, the knot pusher device 50 is assembled with the suture 100 including a pre-tied slip knot 102 with a closable slip loop 104 protruding from the distal end of the central channel 56 at the beveled face 54 of the cannula 52. The slip knot 102 formed in the suture 100 provides a slide end 106 extending through the central channel 56 which is wrapped about the proximal end of the cannula 52 and anchored in the V-shaped slot 62 and slit 64. The slip knot 102 in the suture 100 also provides a free or stay end 108 extending outwardly from the beveled face 54 of the cannula 52.

Referring to FIG. 12, the suture 100 is shown threaded through an anchor 120 for attaching the suture 100 to bone, e.g., in arthroscopic surgery. For example, the anchor 120 can be a wedge-shaped suture anchor of the type disclosed in co-pending U.S. patent application Ser. No. 235,737, entitled "WEDGE SHAPED SUTURE ANCHOR AND METHOD OF IMPLANTATION" filed Jun. 30, 1994, and assigned to Ethicon, Inc., the same assignee of the present invention, which is incorporated herein by reference.

Referring to FIG. 13, the knot pusher device 50 can be used to advance the slip knot 102 along the suture 100 in the following manner. The stay end 108 of the suture 100 is attached to tissue (not shown) and is inserted through the loop 104 of the slip knot 102 which is tightened by pulling the slide end 106 of the suture 100. The slide end 106 is anchored in the notch 62 and slit 64 at the proximal end of the cannula 52 and the stay end 108 is slidably inserted into the longitudinal groove 58 on the longest portion of the cannula 52. The cannula 52 is advanced toward the tissue (not shown) while pulling on the stay end 108 of the suture 100 which slides through the loop 104 of the slip knot 102 in the proximal direction. As a result, the slip knot 102 is advanced in the distal direction by the beveled face 54 of the cannula 52 as the stay end 108 is pulled in the distal direction. Similarly, the slip knot 102 can be advanced by inserting the stay end 108 in the longitudinal groove 60 on the shortest portion of the cannula 52 and by pulling the stay end 108 in the proximal direction while the cannula 52 is advanced in the distal direction.

Figure 14:
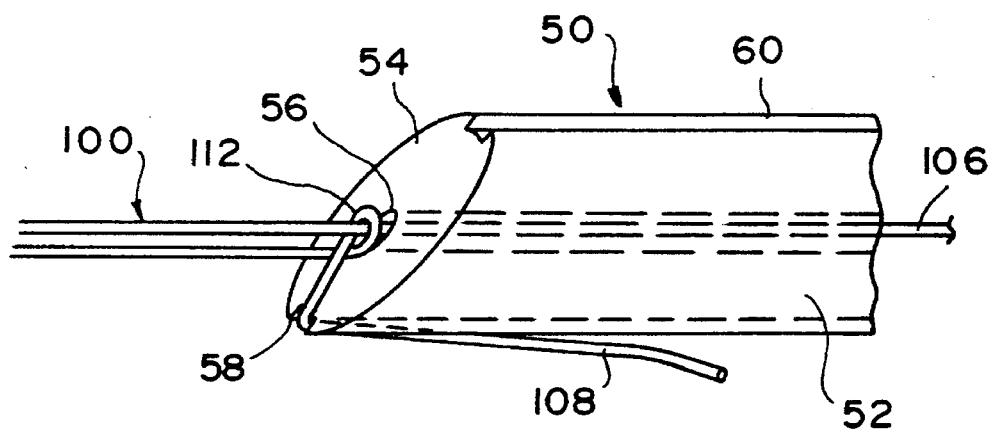
FIG. 14 is an enlarged perspective view of a first loop or throw in the suture engaged by the distal end of the knot pusher device of FIG. 11.
Figure 15:
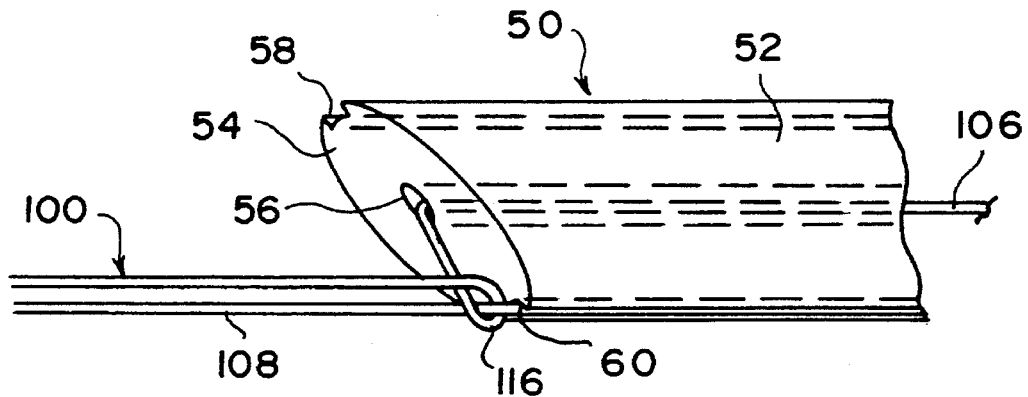
FIG. 15 is an enlarged perspective view of a second loop or throw in the suture engaged by the distal end of the knot pusher device of FIG. 11.

Referring to FIGS. 14 and 15, in the use of the knot pusher device 50 to form additional knots or throws in the suture 100, the configuration of the knots can be controlled by the orientation of the beveled face 54 and the longitudinal grooves 58 and 60 of the cannula 52. For example, as shown in FIG. 14, a simple half-hitch knot is formed by looping the stay end 108 over the slide end 106 of the suture 100 to form a loop or throw 112. Then, by inserting the stay end 108 of the suture 100 into the longitudinal groove 58 along the longest portion of the cannula 52 and by advancing the beveled face 54 of the cannula 52 to engage the loop or throw 112, the slide end 106 of the suture 100 becomes the post strand and the stay end 108 becomes the loop strand of the knot. As shown in FIG. 15, by inserting the stay end 108 in the longitudinal groove 60 along the shortest portion of the cannula 52 and by advancing the beveled face 54 of the cannula 52 to engage the knot, the slide end 106 becomes the loop strand and the stay end 108 becomes the post strand of the knot. As a result, a loop 116 is formed on the slide end 106 instead of the stay end 108 of the suture 100. The alternating use of the slide end 106 and the stay end 108 as the post and loop strands in the formation of additional throws enhances the strength of the completed knot and reduces the tendency of the knot to slip.

As shown in FIG. 16, in a method of forming surgical knots using the knot pusher device 50, the free or stay end 108 of the suture 100 is attached to a portion of internal body tissue 110 which is to be sutured or re-attached to bone or other internal body tissue (not shown). For example, if the tissue 110 is to be sutured, the suture end 108 can be inserted through the tissue 110 by a surgical needle (not shown). Alternatively, if the tissue 110 is to be ligated, the suture end 108 can be wrapped about the tissue 110.

Referring to FIG. 16, after the suture 100 is attached to the tissue 110, the stay end 108 is retrieved through the surgical port 90, e.g., by a forceps or grasper. Then, as shown in FIG. 17, the stay end 108 which extends outwardly from the surgical port 90 is threaded through the pre-formed loop 104 of the slip knot 102.

Next, as shown in FIG. 18, the slide end 106 of the slip knot 102 is released from the notch 62 at the proximal end of the cannula 52. The loop 104 is reduced in size by pulling the slide end 106 of the slip knot 102 in the proximal direction to provide a snug fit around the stay end 108. Then, the slide end 106 of the suture 100 is replaced in the notch 62 at the proximal end of the cannula 52.

Next, as shown in FIG. 19, the cannula 52 is advanced into the surgical port 90 toward the tissue 110 while pulling on the stay end 108 of the suture 100 which slides through the loop 104 of the slip knot 102. When the slip knot 102 is moved adjacent to the tissue 110 to be re-attached, the approximation of the tissue 110 can be controlled by using the beveled face 54 at the distal end of the cannula 52 in a spatula-like manner and by applying additional tension to the stay end 108 of the suture 100. With the tissue 110 in the proper position and the tension maintained on the stay end 108, tension is applied to the slide end 106 (FIG. 20) of the suture 100 to tighten the loop 104 completely to secure the slip knot 102 to the tissue 110.

Referring to FIG. 21, to form additional knots (throws) behind the slip knot 102, the slide end 106 of the suture 100 is released from the notch 62 and the cannula 52 is withdrawn from the surgical port 90. Preferably, the slide end 106 of the suture 100 remains slidably received in the central channel 56 of the cannula 52. Next, as shown in FIG. 22, an additional loop or throw 112 is made by looping the stay end 108 over then under the slide end 106 of the suture 100. The stay end 108 of the suture 100 is slidably inserted into the longitudinal groove 58 on the longest portion of the outer cylindrical surface of the cannula 52. The loop 112 is engaged by the beveled face 54 of the cannula 52. Then, as shown in FIG. 23, while maintaining tension on both ends 106 and 108 of the suture 100, the cannula 52 is advanced into the surgical port 90 to push the loop 112 toward the tightened slid knot 102. The loop 112 formed in the stay end 108 is advanced adjacent to the slip knot 102.

Referring to FIG. 24, the slide end 106 of the suture 100 is released from the notch 62 and the cannula 52 is again withdrawn from the surgical port 90. Preferably, the slide end 106 of the suture 100 remains slidably received in the central channel 56 of the cannula 52. Next, another loop or throw 114 is made by looping the stay end 108 over then under the slide end 106 of the suture 100. With the cannula 52 rotated by 180° about its longitudinal axis, the stay end 108 of the suture 100 is slidably inserted into the longitudinal groove 60 along the shortest portion of the outer cylindrical surface of the cannula 52. The loop 114 is engaged by the beveled face 54 of the cannula 52. Then, as shown in FIG. 25, while maintaining tension on both ends 106 and 108 of the suture 100, the cannula 52 is inserted into the surgical port 90 and advanced toward the tightened slip knot 102. Because of the tension applied to the stay end 108, the loop 114 (FIG. 24) is untwisted as the cannula 52 is advanced and in its place a loop 116 (FIG. 25) is formed in the slide end 106 of the suture 100. After the loop 116 is advanced adjacent to the loop 112 by the cannula 52, the loop 116 is tightened by pulling on the suture ends 106 and 108.

By alternating the steps shown in FIGS. 24 and 25, the loops or throws 112 and 116 can be alternately formed on the stay end 108 and the slide end 106 of the suture 100. This procedure forms a surgical knot with a configuration which is enhanced in strength and resistance to slippage.

As shown in FIG. 26, in a method of forming surgical knots in arthroscopic surgery, a bone, generally 122, is prepared by drilling a hole 124 through its outer layer or cortex 126 into its inner cortical layer 128. The wedge-shaped anchor 120 with the attached suture 100 is inserted into the drilled hole 124 with the suture end 108 extending outwardly from the body through the surgical port (not shown). For example, the anchor 120 can be inserted and anchored in the hole 124 using the type of installation tool disclosed in co-pending U.S. patent application Ser. No. 235,737, entitled "WEDGE SHAPED SUTURE ANCHOR AND METHOD OF IMPLANTATION" filed Jun. 30, 1994 and assigned to Ethicon, Inc., the same assignee of the present invention.

Next, as shown in FIG. 27, a needle 130 is inserted through a ligament 132 to be re-attached to the bone 122. The needle 130 has a hook 134 at its distal end which is manipulated to capture the stay end 108 of the suture 100. Then, as shown in FIGS. 28 and 29, the needle 130 is withdrawn from the surgical port (not shown) to pull the stay end 108 of the suture through the ligament 132.

Referring to FIG. 30, the stay end 108 of the suture 100 which extends outwardly from the surgical port (not shown) is threaded through the pre-formed loop 104 of the slip knot 102. Next, the slide end 106 of the slip knot 102 is released from the notch 62 at the proximal end of the cannula 52. The loop 104 is reduced in size by pulling the slide end 106 of the slip knot 102 in the proximal direction to provide snug fit around the stay end 108 (FIG. 31). Then, the slide end 106 of the suture 100 is replaced in the notch 62 at the proximal end of the cannula 52.

Next, as shown in FIG. 31, the cannula 52 is advanced toward the ligament 132 while pulling on the stay end 108 of the suture 100 which slides through the loop 104 of the slip knot 102. As the stay end 108 of the suture 100 slides through the anchor 120, the slip knot 102 is moved adjacent to the ligament 132 to draw the ligament 132 against the bone 122. The approximation of the ligament 132 to the bone 122 can be controlled by using the beveled face 54 of the cannula 52 in a spatula-like manner and applying additional tension to the stay end 108 of the suture 100. With the ligament 132 in the proper position on the bone 122 and the tension maintained on the stay end 108, tension is applied to the slide end 106 of the suture 100 to tighten the loop 104 completely to secure the slip knot 102 to the ligament 132.

Referring to FIG. 32, to form additional knots (throws) behind the slip knot 102, the cannula 52 is withdrawn from the surgical site with the slide end 106 of the suture 100 released from the notch 62. Preferably, the slide end 106 of the suture 100 remains slidably received in the central channel 56 of the cannula 52. Next, an additional loop or throw 136 is made by looping the stay end 108 over then under the slide end 106 of the suture 100. The stay end 108 of the suture 100 is slidably inserted into the longitudinal groove 58 on the longest portion of the outer cylindrical surface of the cannula 52. The loop 136 is engaged by the beveled face 54 of the cannula 52. Then, while maintaining tension on both ends 106 and 108 of the suture 100, the cannula 52 is advanced toward the surgical site to push the loop 136 toward the tightened slip knot 102.

Referring to FIG. 33, the next loop or throw 138 can be formed on the slide end 106, instead of the stay end 108, by rotating the cannula 52 by 180° about its longitudinal axis and inserting the stay end 108 of the suture 100 into the longitudinal groove 60 extending along the shortest portion of the outer cylindrical surface of the cannula 52. The loop 138 is engaged by the beveled face 54 of the cannula 52. Then, while maintaining tension on both ends 106 and 108 of the suture 100, the cannula 52 is inserted into the surgical port 90 to push the loop 138 toward the tightened loop 104 of the slip knot 102.

By alternating the steps shown in FIGS. 32 and 33, the loops or throws 136 and 138 can be alternately formed on the stay end 108 and the slide end 106 of the suture 100. This procedure results in a knot configuration which exhibits enhanced strength and resistance to slippage.

Referring to FIG. 34, the knot pusher device 50 can be employed in arthroscopic surgery on a shoulder joint where it is desired to re-attach a ligament, e.g., the glenoid labrum 140, to the rim of the glenoid bone 142 which adjoins the head of the humerus 144. A suture anchor 120 is anchored in a hole 146 drilled into the rim of the glenoid bone 142. The suture 100 is attached to the glenoid labrum 140 and passed through the slip knot 102 which is tightened against the beveled face 54 of the cannula 52. The knot pusher device 50 is inserted into the surgical port 90 to advance the slip knot 102 toward the glenoid labrum 140. The desired placement of the knot 102 on the glenoid labrum 140 can be controlled by the orientation of the beveled face 54 of the cannula 52. Preferably, the knot 102 is positioned on the underside of the glenoid labrum 140 away from the joint between the rim of the glenoid bone 142 and the head of the humerus 144. The beveled face 54 of the cannula 52 also permits the glenoid labrum 140 to be lifted to the desired position on the rim of the glenoid bone 142 by manipulation of the cannula 52. After the knot 102 is placed in the desired position on the glenoid labrum 140, additional knots or throws are formed in the suture 100 as previously described.

The invention in its broader aspects is not limited to the specific details of the preferred embodiments shown and described, and those skilled in the art will recognize that the invention can be practiced with modification within the spirit and scope of the appended claims.

We claim:

1. A surgical knot pusher device for advancing knots formed in a suture, comprising:

a cannula having a beveled face at its distal end for engaging a knot formed by the ends of one or more sutures and a channel extending axially therethrough and terminating at said beveled face for slidably receiving one suture end; and a pair of longitudinal grooves formed on an outer surface of said cannula, each of said grooves intersecting the periphery of said beveled face for slidably receiving another suture end.

2. The knot pusher device of claim 1, wherein:

said beveled face of said cannula has an elliptical configuration.

3. The knot pusher device of claim 1, which includes:

a threading element slidably inserted in said channel for threading one suture end into said cannula.

4. The knot pusher device of claim 1, wherein:

said beveled face is slanted at an angle in the range of 15° to 75° relative to the longitudinal axis of said cannula.

5. The knot pusher device of claim 1, wherein:

said beveled face is slanted at about 40° relative to the longitudinal axis of said cannula.

6. A method of forming a knot in a suture attached to internal body tissue at a surgical site inside a body using a knot pusher device comprising a cannula having a beveled face at its distal end, a channel extending axially therethrough and a longitudinal groove formed on an outer surface of the cannula and intersecting the periphery of the beveled face, said method comprising the steps of:

attaching the suture to the internal body tissue with the suture ends extending outwardly from the body;

forming a slidable knot in the suture ends outside of the body;

inserting one suture end into the channel and the other suture end into the longitudinal groove of the knot pusher device; and advancing the knot pusher device toward the surgical site with the slidable knot engaged by the beveled face of the knot pusher device while one suture end slides along the longitudinal groove of the knot pusher device to advance the knot along the suture and tighten the knot against the tissue.

7. The method of claim 6, wherein:

said slidable knot is a slip knot including a slide end, a stay end and a closable slip loop; and said slide end is inserted into the channel of said cannula and said stay end is inserted into the longitudinal groove of the cannula.

8. A method of forming a knot in a suture attached to internal body tissue at a surgical site inside a body using a knot pusher device comprising a cannula having a beveled face at its distal end, a channel extending axially therethrough and a longitudinal groove formed on an outer surface of the cannula and intersecting the periphery of the beveled face, said method comprising the steps of:

attaching the suture to the internal body tissue with the suture ends extending outwardly from the body;

forming a slidable knot in the suture ends outside of the body;

inserting one suture end into the channel and the other suture end into the longitudinal groove of the knot pusher device; and advancing the knot pusher device toward the surgical site with the slidable knot engaged by the beveled face of the knot pusher device while the suture ends slide along the channel and the longitudinal groove of the knot pusher device to advance the knot along the suture and tighten the knot against the tissue.

9. The method of claim 8, wherein:

the longitudinal groove extends along the longest portion of the outer surface of the cannula; and the suture end received in the channel becomes the post end of the knot and the suture end received in the longitudinal groove becomes the loop end of the knot when the knot is engaged by the beveled face of the cannula.

10. The method of claim 8, wherein:

the longitudinal groove extends along the shortest portion of the outer surface of the cannula; and the suture end received in the channel becomes the loop end of the knot and the suture end received in the longitudinal groove becomes the post end of the knot when the knot is engaged by the beveled face of the cannula.

11. A method of forming a knot in a suture attached to internal body tissue at a surgical site inside a body using a knot pusher device comprising a cannula having a beveled face at its distal end, a channel extending axially therethrough and a pair of longitudinal grooves formed on an outer surface of the cannula and intersecting the periphery of the beveled face, one of the longitudinal grooves being located on the longest portion of the cannula and the other longitudinal groove being located on the shortest portion of the cannula, said method comprising the steps of:

attaching the suture to the internal body tissue with the suture ends extending outwardly from the body;

threading a first suture end into the channel of the knot pusher device;

forming a first slidable knot by looping the second suture end over the first suture end outside of the body;

inserting the second suture end into one of the longitudinal grooves of the knot pusher device;

advancing the knot pusher device toward the surgical site with the first slidable knot engaged by the beveled face of the knot pusher device while the first suture end slides along the channel and the second suture end slides along one of the longitudinal grooves of the knot pusher device to advance the first knot along the suture and tighten the first knot against the tissue;

withdrawing the knot pusher device from the surgical site with the first suture end remaining threaded in the channel;

forming a second slidable knot by looping the second suture end over the first suture end outside of the body;

inserting the second suture end into the other longitudinal groove of the knot pusher device;

advancing the knot pusher device toward the surgical site with the second slidable knot engaged by the beveled face of the knot pusher device while the first suture end slides along the channel and the second suture end slides along the other longitudinal groove of the knot pusher device to advance the second knot along the suture and tighten the second knot against the tissue.

12. The method of claim 11, wherein:

the first suture end received in the channel becomes the post end of the knot and the second suture end received in the longitudinal groove along the longest portion of the cannula becomes the loop end of the Knot when the knot is advanced.

13. The method of claim 12, wherein:

the first, suture end received in the channel becomes the loop end of the knot and the second suture end received in the longitudinal groove along the shortest portion of the cannula becomes the post end of the knot when the knot is advanced.

\* \* \* \* \*